(12) United States Patent
Gittings et al.

(10) Patent No.: US 6,361,557 B1
(45) Date of Patent: Mar. 26, 2002

(54) STAPLEBUTTON RADIOPAQUE MARKER

(75) Inventors: Darin C. Gittings, Sunnyvale; Denise M. DeMarais, San Jose, both of CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 09/497,372

(22) Filed: Feb. 3, 2000

Related U.S. Application Data

(60) Provisional application No. 60/118,576, filed on Feb. 5, 1999.

(51) Int. Cl.⁷ .................................................. A61F 2/06
(52) U.S. Cl. .................. 623/1.13; 623/1.34; 606/75; 606/151; 606/157
(58) Field of Search ............................... 623/1.13, 1.34; 606/151, 157, 75; 411/487–494, 466–468, 471, 472

(56) References Cited

U.S. PATENT DOCUMENTS

| 66,968 A | * 7/1867 | Kendig ...................... 411/471 |
| 269,882 A | 1/1883 | Reed |

(List continued on next page.)

FOREIGN PATENT DOCUMENTS

| EP | 0 146 699 | 7/1985 |
| EP | 0 421 729 | 4/1991 |
| EP | 0 480 667 | 4/1992 |
| EP | 0 508 473 | 10/1992 |
| EP | 0 517 075 | 12/1992 |
| EP | 0 519 214 | 12/1992 |
| EP | 0 519 604 | 12/1992 |
| EP | 0 649 637 | 4/1995 |
| EP | 0 669 114 | 8/1995 |
| EP | 0 679 372 | 11/1995 |
| EP | 0 680 734 | 11/1995 |
| EP | 0 684 022 | 11/1995 |
| EP | 0 686 379 | 12/1995 |
| EP | 0 699 423 | 3/1996 |
| EP | 0 709 068 | 5/1996 |
| EP | 0 850 653 | 7/1998 |
| EP | 1 004 327 | 5/2000 |
| EP | 1 025 811 A2 | 8/2000 |
| WO | WO 90/15582 | 12/1990 |
| WO | WO 91/15254 | 10/1991 |
| WO | WO 92/19151 | 11/1992 |
| WO | WO 93/08862 | 5/1993 |

(List continued on next page.)

OTHER PUBLICATIONS

U.S. Appl. No. 09/046,241 entitled "Catheter Having Extruded Radiopaque Stripes Embedded in Soft Tip and Method of Fabrication".

U.S. Appl. No. 09/178,397; Filed: Oct. 23, 1998, entitled, "Implantable Device With Radiopaque Ends".

Primary Examiner—Corrine McDermott
Assistant Examiner—Choon P. Koh
(74) Attorney, Agent, or Firm—Sterne, Kessler, Goldstein & Fox P.L.L.C.

(57) ABSTRACT

Improved endoluminal prostheses and methods for their use, having discrete position indicating elements which facilitate the orienting and deploying of the prostheses within body lumens. The endoluminal prostheses may include endovascular prostheses, often formed as stent-grafts having a flexible tubular liner or "graft." The position indicating elements may include an improved radiopaque image marker to be applied to the graft, before the graft is deployed particularly within branching blood vessels for the treatment of abdominal and other aneurysms. The marker is in the form of a flat metal blank resembling a circular plate or "button." The disk may be fastened or secured on to the graft using a pair of fastening shanks or tangs which extend parallel to each other outward from a surface of the plate.

21 Claims, 9 Drawing Sheets

U.S. PATENT DOCUMENTS

| | | |
|---|---|---|
| 308,368 A | 11/1884 | McGill |
| 3,618,614 A | 11/1971 | Flynn |
| 3,757,768 A | 9/1973 | Kline |
| 4,202,349 A | 5/1980 | Jones |
| 4,279,252 A | 7/1981 | Martin |
| 4,345,602 A | 8/1982 | Yoshimura et al. |
| 4,430,083 A | 2/1984 | Ganz et al. |
| 4,456,017 A | 6/1984 | Miles |
| 4,464,176 A | 8/1984 | Wijayarathna |
| 4,469,483 A | 9/1984 | Becker et al. |
| 4,538,622 A | 9/1985 | Samson et al. |
| 4,545,390 A | 10/1985 | Leary |
| 4,577,637 A | 3/1986 | Mueller, Jr. |
| 4,588,399 A | 5/1986 | Nebergall et al. |
| 4,617,932 A | 10/1986 | Kornberg |
| 4,619,274 A | 10/1986 | Morrison |
| 4,636,346 A | 1/1987 | Gold et al. |
| 4,657,024 A | 4/1987 | Coneys |
| 4,662,404 A | 5/1987 | LeVeen et al. |
| 4,721,117 A | 1/1988 | Mar et al. |
| 4,757,827 A | 7/1988 | Buchbinder et al. |
| 4,763,647 A | 8/1988 | Gambale |
| 4,793,359 A | 12/1988 | Sharrow |
| 4,796,637 A | 1/1989 | Mascuch |
| 4,798,598 A | 1/1989 | Bonello et al. |
| 4,815,478 A | 3/1989 | Buchbinder et al. |
| 4,817,613 A | 4/1989 | Jaraczewski et al. |
| 4,821,722 A | 4/1989 | Miller et al. |
| 4,846,186 A | 7/1989 | Box et al. |
| 4,867,174 A | 9/1989 | Skribiski |
| 4,873,983 A | 10/1989 | Winters |
| 4,884,579 A | 12/1989 | Engelson |
| 4,886,062 A | 12/1989 | Wiktor |
| 4,895,168 A | 1/1990 | Machek |
| 4,898,591 A | 2/1990 | Jang et al. |
| 4,906,244 A | 3/1990 | Pinchuk et al. |
| 4,922,924 A | 5/1990 | Gambale et al. |
| 4,938,220 A | 7/1990 | Mueller, Jr. |
| 4,957,110 A | 9/1990 | Vogel et al. |
| 4,981,470 A | 1/1991 | Bombeck, IV |
| 4,990,138 A | 2/1991 | Bacich et al. |
| 5,034,005 A | 7/1991 | Appling |
| 5,040,543 A | 8/1991 | Badera et al. |
| 5,045,072 A | 9/1991 | Castillo et al. |
| 5,063,935 A | 11/1991 | Gambale |
| 5,065,769 A | 11/1991 | de Toledo |
| 5,069,217 A | 12/1991 | Fleischhacker, Jr. |
| 5,081,997 A | 1/1992 | Bosley, Jr. et al. |
| 5,084,022 A | 1/1992 | Claude |
| 5,095,915 A | 3/1992 | Engelson |
| 5,105,818 A | 4/1992 | Christian et al. |
| RE33,911 E | 5/1992 | Samson et al. |
| 5,129,890 A | 7/1992 | Bates et al. |
| 5,144,959 A | 9/1992 | Gambale et al. |
| 5,147,315 A | 9/1992 | Weber |
| 5,147,317 A | 9/1992 | Shank et al. |
| 5,151,105 A | 9/1992 | Kwan-Gett |
| 5,160,559 A | 11/1992 | Scovil et al. |
| 5,171,232 A | 12/1992 | Castillo et al. |
| 5,174,302 A | 12/1992 | Palmer |
| 5,176,149 A | 1/1993 | Grenouillet |
| 5,178,158 A | 1/1993 | de Toledo |
| 5,184,627 A | 2/1993 | de Toledo |
| 5,209,730 A | 5/1993 | Sullivan |
| 5,211,636 A | 5/1993 | Mische |
| 5,221,270 A | 6/1993 | Parker |
| 5,228,453 A | 7/1993 | Sepetka |
| 5,234,416 A | 8/1993 | Macaulay et al. |
| 5,250,034 A | 10/1993 | Appling et al. |
| 5,253,653 A | 10/1993 | Daigle et al. |
| 5,256,158 A | 10/1993 | Tolkoff et al. |
| 5,259,393 A | 11/1993 | Corso, Jr. et al. |
| 5,267,574 A | 12/1993 | Viera et al. |
| 5,275,622 A | 1/1994 | Lazarus et al. |
| 5,300,025 A | 4/1994 | Wantink |
| 5,300,048 A | 4/1994 | Drewes, Jr. et al. |
| 5,342,348 A | 8/1994 | Kaplan |
| 5,366,442 A | 11/1994 | Wang et al. |
| 5,366,473 A | 11/1994 | Winston et al. |
| 5,366,504 A | 11/1994 | Andersen et al. |
| 5,387,235 A | 2/1995 | Chuter |
| 5,403,292 A | 4/1995 | Ju |
| 5,405,004 A | 4/1995 | Vest et al. |
| 5,419,324 A | 5/1995 | Dillow |
| 5,429,597 A | 7/1995 | DeMello et al. |
| 5,429,617 A | 7/1995 | Hammersmark et al. |
| 5,456,251 A | 10/1995 | Fiddian-Green |
| 5,456,705 A | 10/1995 | Morris |
| 5,458,639 A | 10/1995 | Tsukashima et al. |
| 5,464,438 A | 11/1995 | Menaker |
| 5,470,315 A | 11/1995 | Adams |
| 5,476,508 A | 12/1995 | Amstrup |
| 5,480,383 A | 1/1996 | Bagaoisan et al. |
| 5,484,418 A | 1/1996 | Quiachon et al. |
| 5,485,667 A | 1/1996 | Kleshinski |
| 5,489,277 A | 2/1996 | Tolkoff et al. |
| 5,489,295 A | 2/1996 | Piplani et al. |
| 5,509,910 A | 4/1996 | Lunn |
| 5,542,937 A | 8/1996 | Chee et al. |
| 5,545,138 A | 8/1996 | Fugoso et al. |
| 5,545,151 A | 8/1996 | O'Connor et al. |
| 5,549,552 A | 8/1996 | Peters et al. |
| 5,562,726 A | 10/1996 | Chuter |
| 5,562,728 A | 10/1996 | Lazarus et al. |
| 5,569,221 A | 10/1996 | Houser et al. |
| 5,571,089 A | 11/1996 | Crocker |
| 5,575,817 A | 11/1996 | Martin |
| 5,582,619 A | 12/1996 | Ken |
| 5,584,821 A | 12/1996 | Hobbs et al. |
| 5,599,325 A | 2/1997 | Ju et al. |
| 5,599,326 A | 2/1997 | Carter |
| 5,603,991 A | 2/1997 | Kupiecki et al. |
| 5,609,629 A | 3/1997 | Fearnot et al. |
| 5,658,263 A | 8/1997 | Dang et al. |
| 5,662,675 A | 9/1997 | Stockert et al. |
| 5,683,370 A | 11/1997 | Luther et al. |
| 5,683,449 A | 11/1997 | Marcade |
| 5,683,451 A | 11/1997 | Lenker et al. |
| 5,690,120 A | 11/1997 | Jacobson et al. |
| 5,718,724 A | 2/1998 | Goicoechea et al. |
| 5,725,513 A | 3/1998 | Ju et al. |
| 5,725,572 A | 3/1998 | Lam et al. |
| 5,728,042 A | 3/1998 | Schwager |
| 5,741,327 A | 4/1998 | Frantzen |
| 5,749,920 A | 5/1998 | Quiachon et al. |
| 5,769,819 A | 6/1998 | Schwab et al. |
| 5,769,830 A | 6/1998 | Parker |
| 5,769,882 A | 6/1998 | Fogarty et al. |
| 5,776,180 A | 7/1998 | Goicoechea et al. |
| 5,811,043 A | 9/1998 | Horrigan et al. |
| 5,824,037 A | 10/1998 | Fogarty et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,827,225 A | 10/1998 | Ma Schwab |
| 5,853,400 A | 12/1998 | Samson |
| 5,871,468 A | 2/1999 | Kramer et al. |
| 5,876,376 A | 3/1999 | Schwab et al. |
| 5,891,112 A | 4/1999 | Samson |
| 6,024,763 A | 2/2000 | Lenker et al. |

| | | | | | |
|---|---|---|---|---|---|
| 6,068,622 A | 5/2000 | Sater et al. | WO | WO 95/08966 | 4/1995 |
| 6,102,938 A | 8/2000 | Evans et al. | WO | WO 95/15780 | 6/1995 |
| 6,126,685 A | 10/2000 | Lenker et al. | WO | WO 95/21592 | 8/1995 |
| 6,179,811 B1 | 1/2001 | Fugoso et al. | WO | WO 96/08208 | 3/1996 |
| | | | WO | WO 97/33534 | 9/1997 |
| | | | WO | WO 97/37616 | 10/1997 |
| | | | WO | WO 99/17829 | 4/1999 |

FOREIGN PATENT DOCUMENTS

| | | |
|---|---|---|
| WO | WO 93/19663 | 10/1993 |
| WO | WO 95/03010 | 2/1995 |

\* cited by examiner

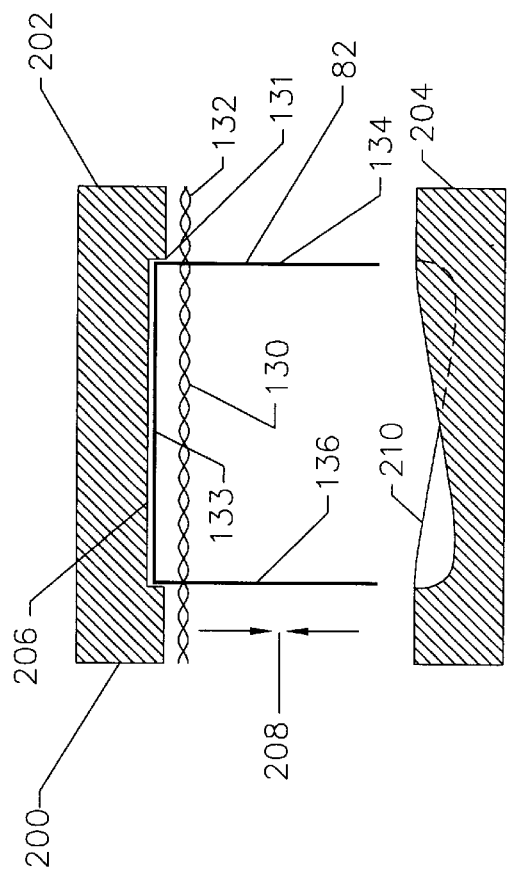
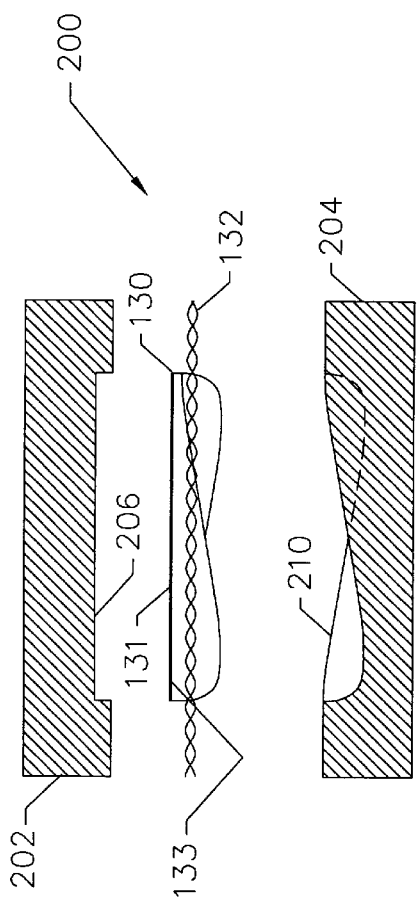

STAPLEBUTTON RADIOPAQUE MARKER

CROSS REFERENCE TO RELATED APPLICATION

This application is based on the following U.S. Provisional Application Ser. No. 60/118,576, filed on Feb. 5, 1999, entitled STAPLEBUTTON RADIOPAQUE MARKER, naming Darin C. Gittings and Denise M. DeMarais as inventors.

BACKGROUND OF THE INVENTION

1. Field of the Invention

The present invention relates generally to tubular prostheses, such as grafts, stents, stentgrafts, and the like. More particularly, the present invention provides endoluminal prostheses having improved position indicating,elements which facilitate orienting and deploying of the prostheses within body lumens, particularly within branching blood vessels for the treatment of abdominal and other aneurysms.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms are most commonly treated in open surgical procedures, where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from undesirable limitations. In particular, proper positioning of an endovascular prosthesis within the vascular system can be problematic.

Accurately positioning and orienting endoluminal prostheses is critical to the efficacy of endovascular aneurysm therapies. These tubular prostheses are generally introduced into the vascular system within a catheter and in a radially compressed configuration, typically being maneuvered into position under fluoroscopy. The positioned prosthesis will radially expand, preferably engaging and sealing against the endolithium of the healthy vessel wall both upstream and downstream of the weakened, distended aneurysm. The prosthesis may expand resiliently when released from the catheter, or may be mechanically expanded, typically using a balloon catheter. In either case, the prosthesis will preferably span the entire aneurysm to prevent pressure from acting on the weakened luminal wall, and to prevent leakage through any rupture of the aneurysm. To provide these advantages, the prosthesis should be axially positioned accurately across the aneurysm so as to isolate the aneurysm from the blood flow through the prosthetic lumen.

Proper radial orientation of endoluminal prostheses is also important, particularly when deploying branching and asymmetric prostheses within the tortuous vascular system. If the branches of branching prostheses are not oriented toward their respective branching body lumens, the surrounding body lumen may be distended to adapt to the misaligned prosthesis, or the prosthetic lumen may be distorted or even closed entirely. For example, if the trunk of a bifurcated prosthesis is deployed with a branch oriented 90° from the iliac arteries (i.e., angling dorsally rather than laterally), the prosthetic branch lumen may fold or kink, and will have to at least bend at a sharp angle to enter the laterally oriented iliac. In fact, as branching prostheses are often assembled in situ, it may not be possible to introduce the branch prosthesis into such a misaligned branch port. As recapture or repositioning of expanded endoluminal prostheses is often problematic, it may even be necessary to resort to an emergency invasive procedure to remedy such misalignment.

Tubular endovascular prostheses are often formed as stent-grafts having a flexible tubular liner or "graft" which is supported by a perforate tubular frame or "stent". The frame perforations define radially expandable structures, while the frame often include metals which are, to some extent, visible under fluoroscopy. To facilitate positioning of endovascular prostheses, it has previously been proposed to coil gold or platinum wires around an element of the perforate frame structure to enhance the visibility of the prosthesis under fluoroscopy. Similarly, it has been suggested that a tube be crimped over an element of the frame. Unfortunately, affixing such structures to the frame may limit or interfere with the radial compressibility of the prosthesis. It can also be difficult to identify the portion of the frame having an enhanced image against the backdrop of the frame itself, and to orient the prosthesis properly based on one or more enhanced frame arms. In one very important improvement, U.S. Pat. No. 5,824,042, herein incorporated by reference for all purposes, describes a radiopaque marker having a passage therethrough to facilitate stitching the marker directly to the liner, which overcomes some of the drawbacks suggested above. Unfortunately, attachments of these sutured markers is somewhat expensive.

Alternatively, it has also been suggested to affix radiopaque lines or image markers to bifurcated grafts in the form of fine wire or chain, either woven into the cloth or applied after weaving, or as an inert paint or plastic. However, the liners of endoluminal prostheses should remain highly flexible, typically being folded when the prosthesis is compressed and unfolding during deployment. Wires, chains, or paints which are sufficiently flexible will generally provide only limited-contrast images when the graft is supported by the obscuring frame, and may become detached from the prosthesis once deployed in the body lumen. Moreover, imaging of such thin, flexible, low-contrast markers is particularly difficult when the prosthesis is in the high density, radially compressed configuration and disposed within a catheter, as is generally required for intravascular maneuvering.

For these reasons, it would be desirable to provide improved endoluminal prostheses and methods for their use. It would be particularly desirable to provide endoluminal prostheses having high-contrast orientation indicating imaging markers which do not interfere with radial compression or expansion, and which are securely and reliably attached to the prosthesis without using sutures, adhesives, and/or weaves. It would further be desirable if such markers could clearly indicate both the position and orientation of the prosthesis, ideally while the prosthesis remains compressed in the delivery catheter, but without substantially increasing the size of the delivery system and/or incurring the high costs of known marker attachment techniques.

2. Description of the Background Art

U.S. Pat. No. 5,824,037, the full disclosure of which is hereby incorporated by reference, describes modular prostheses and prosthetic construction methods. Application Ser. No. 08/104,960, filed Aug. 29, 1996 (Attorney-Docket No. 16380-003410), also incorporated herein by reference, describes bifurcated modular prosthetic structures and in situ methods for their assembly.

Published PCT patent application WO 95/21,592 describes a bifurcated endoluminal prosthesis including a bifurcated stent and a second stent. U.S. Pat. No. 5,387,235 describes a bifurcated graft having radiopaque lines and markers. U.S. Pat. No. 5,776,180 describes stents which include fabric coverings and radiopaque markers formed of wire crimped on the end of a stent or a tube disposed around a length of a wire on the stent.

SUMMARY OF THE INVENTION

The present invention provides improved endoluminal prostheses (and methods for their use) having discrete position indicating elements which facilitate the orienting and deploying of the prostheses within body lumens. More specifically, the endoluminal prostheses includes endovascular prostheses, often formed as stent-grafts, having an improved radiopaque image marker to be applied to the graft before the graft is deployed. Typically, the marker is in the form of a flat metal plate resembling a circular disk or "button," however, the shape of the plate may be modified as desired to conform to the needs of the application. The plate may be fastened or secured on to the graft at any desired position using a pair of fastening shanks or tangs which extend parallel to each other outward from a major surface of the plate, in a fashion similar to the fastening shanks of a common staple. The marker, herein referred to as a "staplebutton" marker, is operated by forcing the fastening shanks through the graft liner, until an underside of the button rests on the liner. Each shank is then folded down on the other side of the liner, so as to bind the material between the folded fastening shanks and the button.

The staplebutton thus described provides a high-contrast, orientation indicating imaging marker, which does not interfere with radial compression or expansion of an endoluminal prostheses on which it is being used. By using fastening shanks or tangs, the staplebutton can be securely and reliably attached to the liner or any other portion of the prosthesis without fear of the inadvertent detachment of the marker. One other advantage of the liner supported marker element is that the marker element can move out of the way of the frame with the liner when the prosthesis is compressed and further, it remains out of the way when the liner (and frame) is deployed. The staplebutton marker can also clearly indicate both the position and orientation of the prosthesis, while the prosthesis remains compressed in the delivery catheter, but without substantially increasing the size of the delivery system.

In a first aspect, the present invention provides a tubular graft comprising a polyester fabric and an imagable body disposed on the liner. The body includes a plate and at least two shanks integral with the plate, the shanks affixing the imagable body on the liner. The imagable body provides a sharp contrast so as to indicate the liner position when the prosthesis is imaged within the patient body.

In a preferred aspect, the present invention provides an endoluminal prosthesis for deployment in a body lumen of a patient body. The prosthesis includes a tubular fabric liner having a proximal end, a distal end, and a lumen therebetween. A plurality of imagable bodies are attached to the liner and provide a sharp contrast so as to define a pattern which indicates the prosthesis position when the prosthesis is imaged within the patient body. Each imagable body has a plate and two integral fastening members, which facilitate the attachment of the imagable bodies to the liner.

In another aspect, the present invention provides an endoluminal prosthesis for deployment in a body lumen of a patient body. The prosthesis includes a tubular fabric liner having a proximal end, a distal end, and a lumen therebetween and a radially expandable frame which supports the liner. A plurality of radiopaque marker elements are disposed on the liner. Each marker includes a plate having a first and a second opposed major surface and two fastening members which extend from the second major surface, through the line, and along the plate so that the marker elements are attached to the liner. The marker elements indicate a position of the prosthesis when the prosthesis is imaged within the body lumen.

Advantageously, the imagable bodies described above can be aligned with openings of a perforate frame structure used to support the fabric liner so that at least some of the imagable bodies are visible through the associated openings when the frame is expanded. Advantageously, the markers need not actually be attached to the frame directly. Such imagable bodies are clearly visible when the prosthesis is deployed, and can also be sized to produce distinct images even when the frame is compressed within a delivery catheter, but should not interfere with the radial expansion of the frame during deployment. The imagable bodies optionally comprise a radiopaque material, or may alternatively produce enhanced ultrasound images.

BRIEF DESCRIPTION OF THE DRAWINGS

FIGS. 7A and 7B illustrate a method for installing the radiopaque marker elements to the liner of an endoluminal prosthesis.

DESCRIPTION OF THE SPECIFIC EMBODIMENTS

The present invention provides radially expansible tubular prostheses, particularly grafts, which generally include discrete, marker elements that provide a high-contrast image when viewed under fluoroscopy, ultrasound, or some other surgical imaging modality, so as to facilitate the proper positioning of the prosthesis within a body lumen. The prostheses of the present invention are suitable for a wide variety of therapeutic uses, including grafting portions of the ureter, urethra, trachea, branchi, esophagus, biliary tract, and the like. The present devices and methods will also be useful for the creating of temporary or long term lumens, such as the formation of fistulas.

The prosthetic structures of the present invention will find their most immediate use as endovascular prostheses for the treatment of diseases of the vasculature, particularly aneurysms, stenoses, and the like, and are especially well suited for therapies to treat abdominal aortic aneurysms adjacent the aortal/iliac junction. These prostheses will generally be radially expansible from a narrow diameter configuration to facilitate introduction into the body lumen, typically during surgical cutdown or percutaneous introduction procedures.

The prosthetic structures described hereinbelow will find use in axially uniform cylindrical prostheses, in preassembled bifurcated prostheses, and as prosthetic modules which are suitable for selective assembly either prior to deployment, or in situ. Such selective assembly of prosthetic modules to form a customized endoluminal prosthesis is more filly described in co-pending U.S. patent application Ser. No. 08/704,960 and U.S. Pat. No. 5,824,037 the fill disclosures of which are herein incorporated by reference.

Figure 1A:
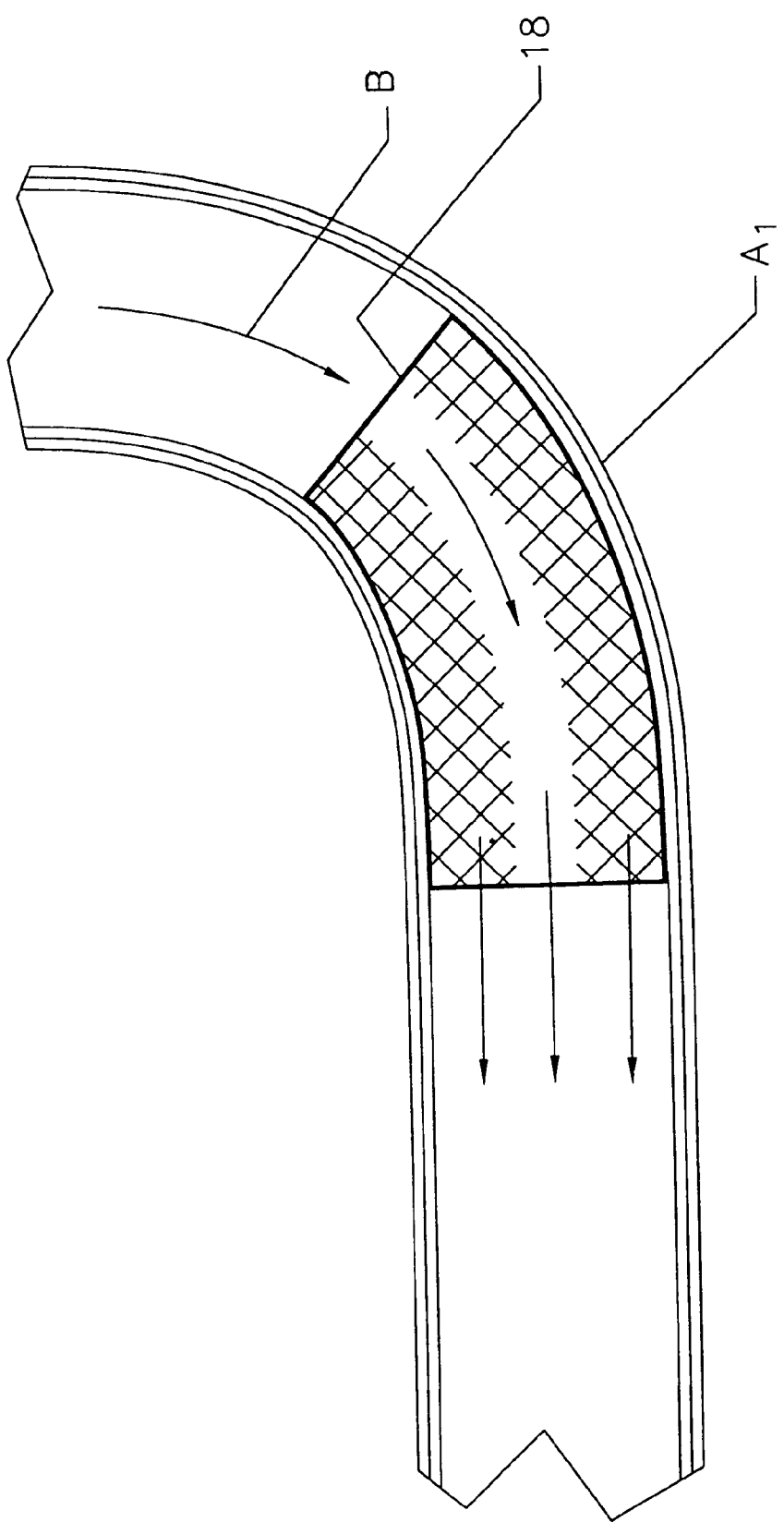
FIG. 1A is a cross-sectional side view of an artery having an exemplary liner having axially constant characteristics.
Figure 1B:
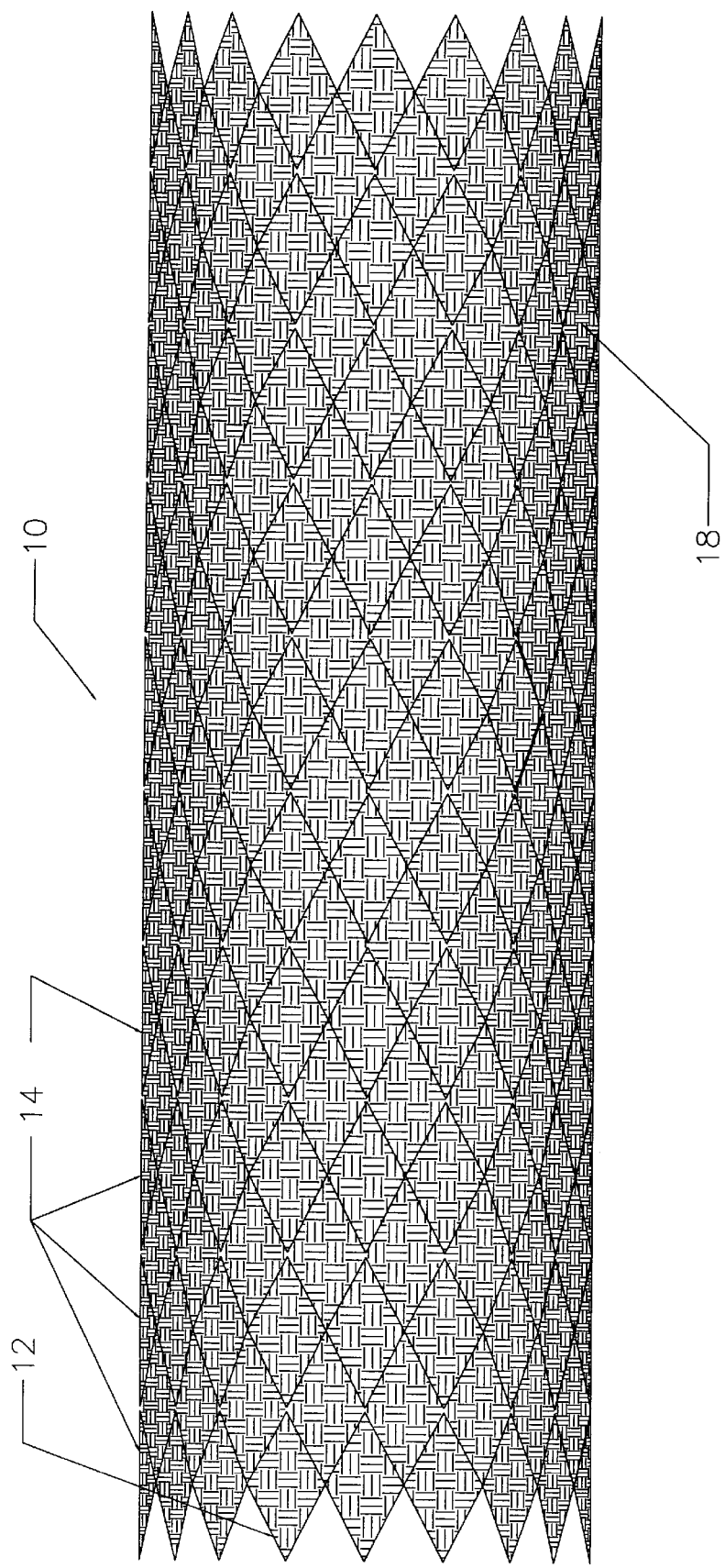
FIG. 1B is a side view of an exemplary cylindrical vascular stent-graft having axially constant characteristics.

An exemplary cylindrical graft structure is shown in FIG. 1A. Artery A1 is shown with its lumen forced open by a form of a tubular graft liner 18, having a proximal end, a distal end, and a graft lumen therebetween. Another exemplary cylindrical graft structure 10 is illustrated in FIG. 1B. Prostheses 10 comprises a perforate tubular frame 12 which includes a plurality of independent (non-connected) ring frames 14. The tubular frame 12 supports an inner liner 18. Optionally, an outer liner is disposed over the ring frames, either inside of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other. The prostheses 10 will typically have a length in the range from about 20 mm to 500 mm, preferably from 50 mm to 200 mm, with a relaxed diameter in the range from about 4 mm to 45 mm, preferably being in the range from about 5 mm to 38 mm.

Figure 2:
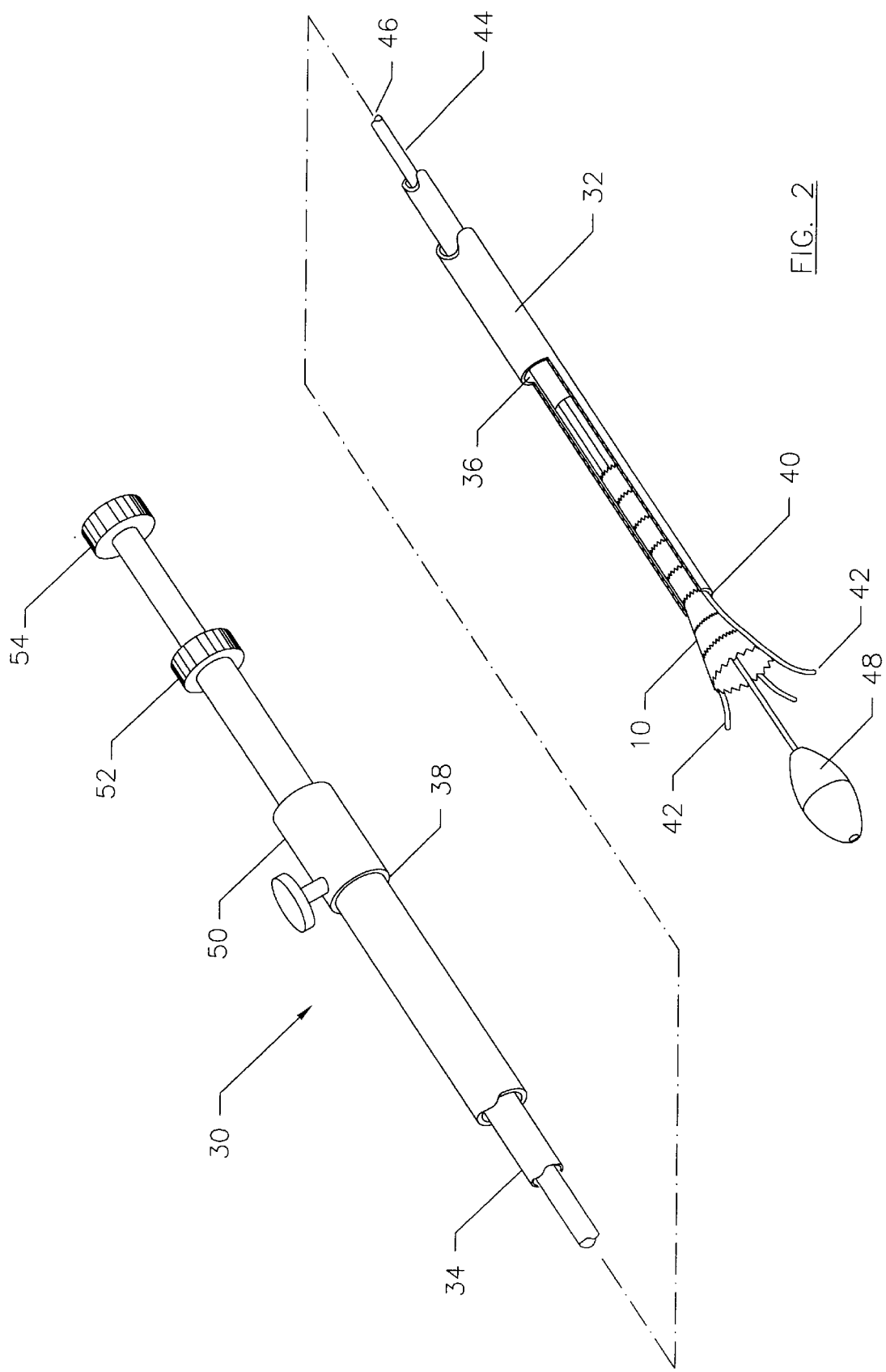
FIG. 2 is a perspective view of an exemplary delivery catheter for use with the prostheses of the present invention, with a portion of the distal end broken away to disclose a prostheses therein.

Referring now to FIG. 2, an exemplary delivery catheter 30 for use with the endoluminal prostheses of the present invention comprises a tubular cover 32 and a shaft 34. Cover 32 has a central lumen 36 extending from a proximal end 38 to a distal end 40. Shaft 34 is slidably received within central lumen 36 and extends proximally of cover 32. A plurality of runners 42 extend distally from shaft 34. Runners 42 line a portion of the inner surface of lumen 36, and slide within the lumen of the shaft. Shaft 34 also has a lumen, in which a core shaft 44 is slidably disposed. Core shaft 44 has a guide wire lumen 46. Nosecone 48 is fixed to the distal end of core shaft 44, and can therefore be manipulated independently of runners 42.

Prostheses 10 is radially compressed and restrained within the plurality of runners 42. In turn, cover 32 prevents runners 42 from expanding outward. Runners 42 are formed from a hard material, and distribute the expansion load of prostheses 10 over the inner surface of central lumen 36. The deploying force is applied proximally against a slider 50 attached to a distal end 38 of cover 30, while holding a luer fitting 52 at the distal end of shaft 34, thereby withdrawing the cover proximally from over the prostheses. An additional luer adapter 54 at the distal end of core shaft 44 allows the core shaft to be manipulated independently, and to be releasably secured to the shaft 34. Exemplary methods and devices for placement of the prostheses of the present invention are more fully described in application Ser. Nos. 081862,085, filed May 22, 1997 and Ser. No. 09/127,666, filed Jul. 31, 1998U.S. Pat. Nos. 5,683,451 and 5,824,041, the full disclosures of which are incorporated herein by reference.

Figure 3:
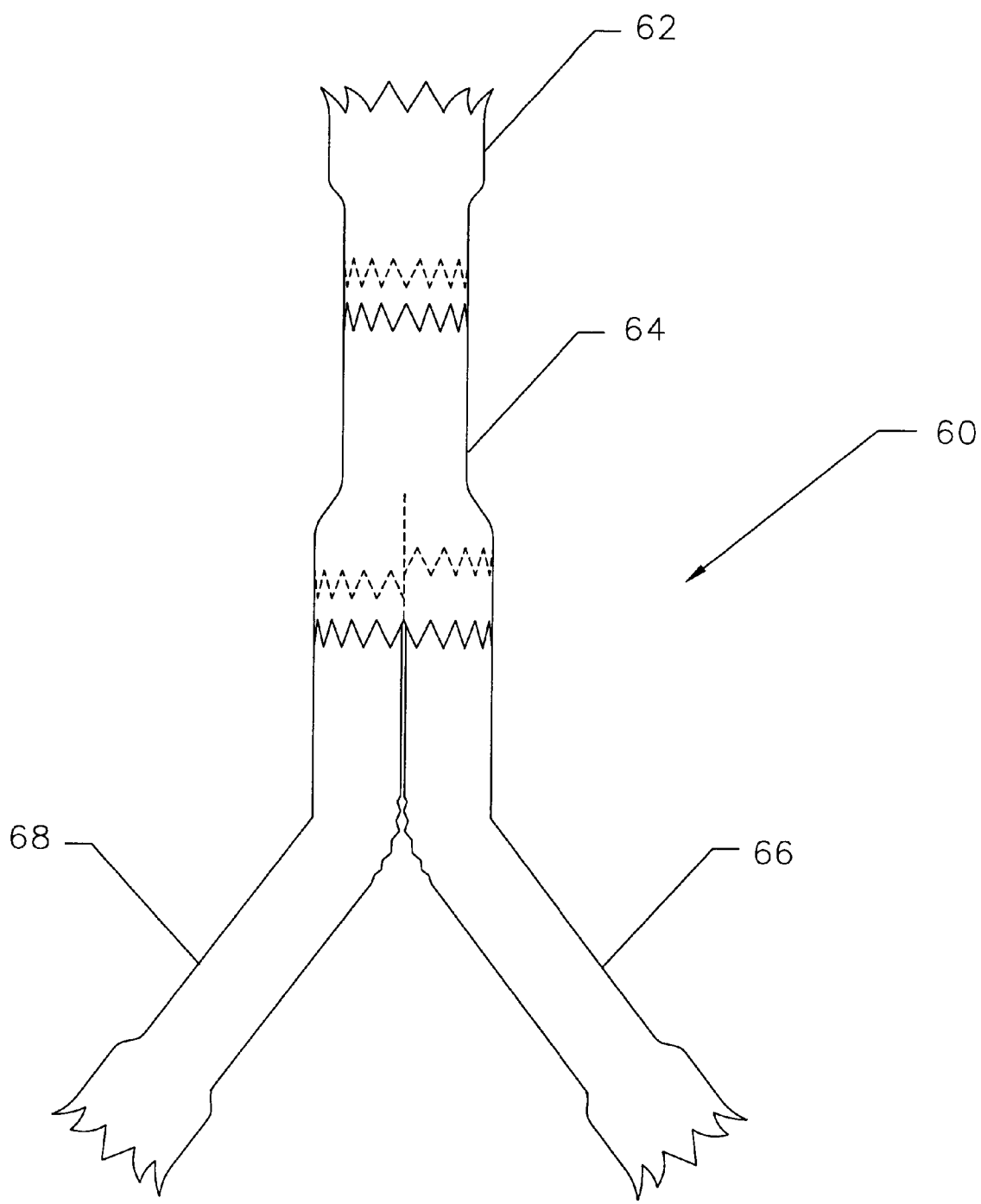
FIG. 3 illustrates a modular branching endoluminal prosthesis assembled from expansible prosthetic modules.

Although the structures and methods of the present invention will at times be described with reference to simple tubular prostheses having a single lumen, it should be understood that the present invention also generally encompasses more complex branching and modular endoluminal prostheses. Referring to FIG. 3, for example, a branching endoluminal stent-graft 60 is assembled from prosthetic modules selected to match the needs of the diseased vascular system of the patient. A common lumen cuffed prosthetic module 62 seals and anchors the assembled prosthesis in the body lumen, typically within the abdominal aorta below the renal arteries and above the left and right iliac arteries. Y-connector module 64 engages cuffed common lumen module 62, and separates the blood flow for the iliac arteries. First angled branching prosthetic module 66 and second angled branching prosthetic module 68 engage the branch lumens of Y-connector module 64 to direct the luminal flow along first and second branching body lumens.

The modular construction and expansible structure of branching prosthesis 60 allows individual tailoring of the common lumen, first branch lumen, and second branch lumen to match the geometry of the body lumen system. For example, a maximum perimeter of common lumen cuffed module 62 may be selected independently of the branching lumen perimeter limits. Additional sealing cuff structures and methods are described in U.S. Pat. No. 5,769,882, the full disclosure of which is also incorporated herein by reference.

Figure 4:
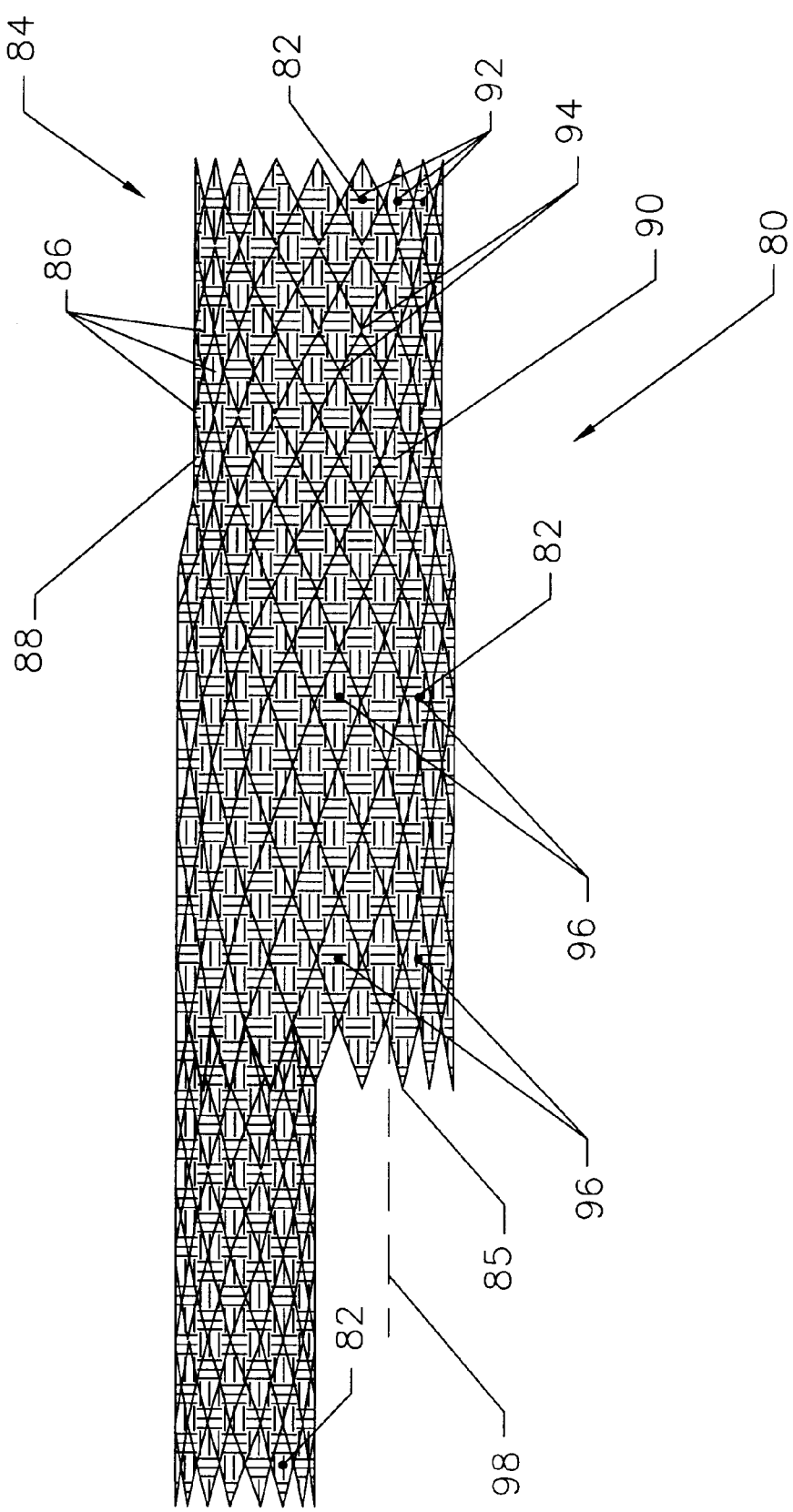
FIGS. 4–5B illustrate orientation indicating stent-grafts having a liner that supports marker elements, the marker elements comprising imagable bodies which define a pattern that facilitates orienting and assembling the prostheses in situ when the prosthesis is imaged fluoroscopically within a body lumen.

Referring now to FIG. 4, an orientation indicating bifurcated prosthesis 80 includes a plurality of discrete marker elements 82 which form an orientation indicating pattern 84 when imaged using fluoroscopy, ultrasound, or other imaging modalities. Such bifurcated prostheses will be particularly useful for reinforcing abdominal aortic aneurysms which extend into one or both iliac arteries, and are typically to be used in combination with a secondary prosthetic module engaging port 85 to seal the port to the body lumen system. Toward that end, pattern 84 preferably indicates the axial location of the ends, and the axial and radial orientation of port 85, when the prosthesis is in a radially compressed configuration within a delivery catheter, and after deployment to assist deploying the secondary prosthesis within port 85.

Minimizing the radial dimensions of the prosthesis significantly facilitates the intravascular maneuvering of the prosthesis during positioning and deployment. Therefore, it is generally desirable that marker elements 82 have the least possible volume to avoid increases in the delivery catheter cross-section. Furthermore, marker elements should not interfere with the radial expansion of the prosthesis from the radially compressed configuration to the radially expanded configuration, during which perforations 86 of frame 88 expand substantially. On the other hand, the pattern should provide a sharp image, despite the fact that frame 88 will often at least partially obscure the pattern when the prosthesis is imaged.

For the above reasons, marker elements 82 are preferably aligned with perforations 86, ideally being substantially disposed within the perforations to maximize their image contrast against the generally radiographically clear liner 90. Generally, supporting the marker elements with the liner, rather than attaching them directly to the frame, also helps avoid interference between the marker elements and the expansion of the surrounding frame structure. Additionally, supporting the marker elements on the liner so that they are separated from the fragile will help to avoid erosion of the frame, as the marker elements will not rub against the frame with physiological movement.

Pattern 84 defined by marker elements 82 includes several novel features. A port orientation indicator 92 is preferably disposed adjacent an end of the prosthesis which will be expanded before the port, and helps to verify that the orientation of port 85 will be aligned properly with the intended branching body lumen before the port is expanded in position. Fine rotational alignment of the prosthesis is facilitated by including roughly opposed marker elements 94, so that the preferred radial orientation of the prosthesis can be provided by orienting the imaging mechanism relative to the body lumen system.

A still further feature of pattern 84 is the two axially separated gates 96 adjacent port 85. The axial positions and separation of these gates gives a visual indicator of the allowable prosthetic module overlap when the prosthesis is deployed and imaged in situ. Modular prostheses having less than a predetermined overlap may not be adequately fixed together, while branches which extend too far into the bifurcated prosthesis may lead to an imbalance in the flow between the branches, or may even fold over and substantially block the luminal flow to one or both branches.

Generally, an overlap is acceptable when an end (or an associated overlap marker) of a secondary prosthesis is disposed between the gates. Advantageously, the gates are defined by markers on either side of the port centerline, greatly improving the visibility of the markers when the delivery catheter of a secondary prosthesis enters the port. Furthermore, a pattern including such gates provides a clear demarcation of the target path between the markers when advancing a guidewire and/or a delivery catheter into the port 85 of bifurcated prosthesis 80.

Figure 5A:
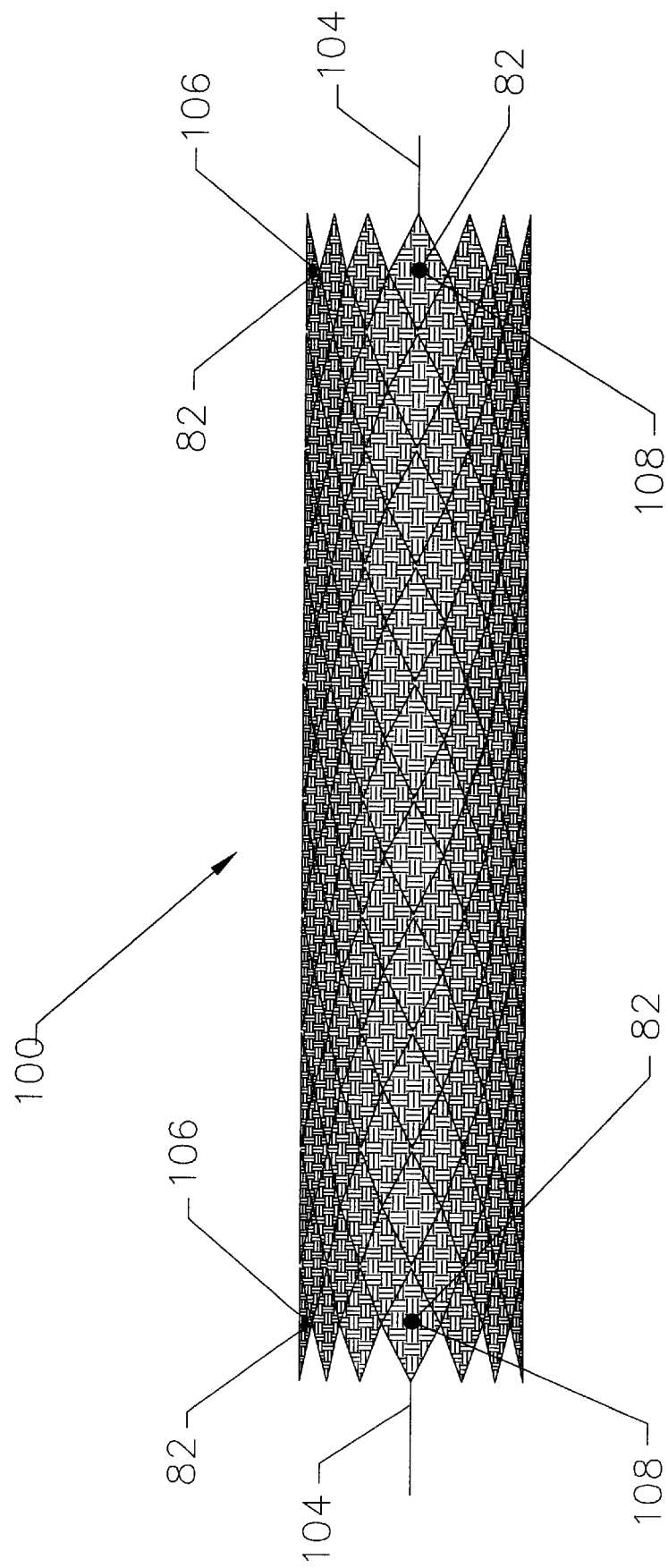
Figure 5B:
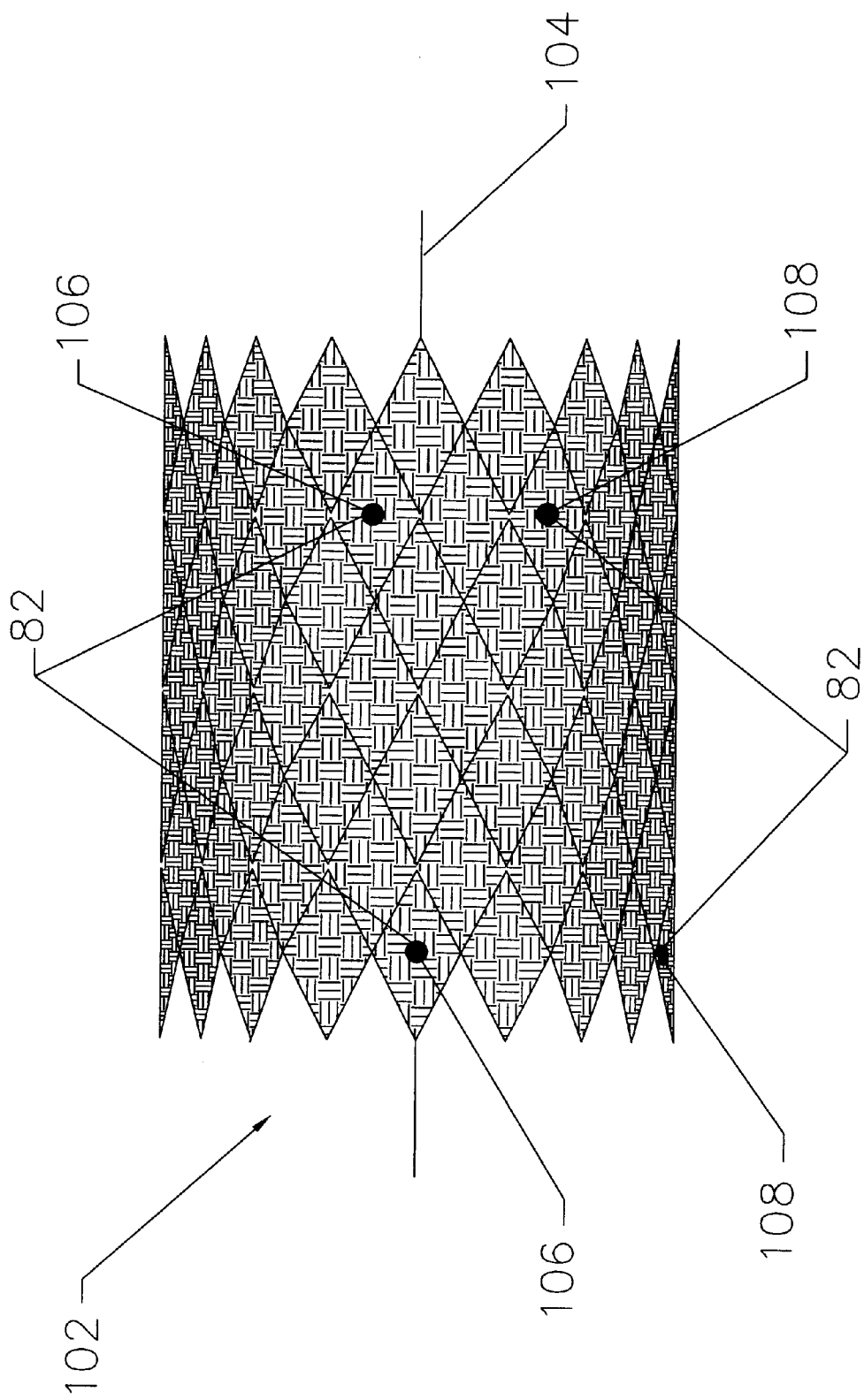

Referring now to FIGS. 5A and 5B, branch secondary prosthetic module 100 and trunk secondary prosthetic module 102 also include image markers 82 which define patterns to facilitate axially positioning and radially orienting these modules within a body lumen, particularly with reference to bifiircated prosthesis 80 described above.

Each of branch module 100 and trunk module 102 include marker elements 106 which produce an image which is aligned along a prosthetic centerline 104 when the prosthesis is properly positioned relative to the imaging apparatus. Advantageously, such a marker element may be aligned with a guidewire passing through the prosthetic lumen even if no other rotational alignment marker is provided, thereby minimizing the total number of markers. Asymmetric marker elements 108 are radially offset from the centerline markers, preferably defining a radial angle between about 15° and 70° with centerline markers 106, to ensure that the modules are not 180° out of rotational alignment, which could be problematic if the modules have a preferred bend angle or some other asymmetric structure. A roughly 30° radial angle is preferred, as flat thin marker elements will produce smaller images when viewed edge-on that tend to blend into the frame as the angle approaches 90°, while smaller angles will be difficult to differentiate. Furthermore, such significantly off-centerline markers are less likely to be overshadowed by subsequent guidewire or delivery catheter placements. Left and right off-centerline markers may be included to ensure the prosthesis is not roughly 150° out of rotational alignment. The asymmetric marker elements can also easily be aligned with the port indicator markers 92 or otherwise consistently aligned with some other imagable structure of the bifurcated prosthesis of FIG. 5A.

Regardless of the specific radiopaque marker alignment or structure selected, the prostheses of the present invention will often include different materials for the frame and for the marker elements. As described above, the frame material will often comprise a high strength metal, while the marker elements will generally comprise a radiopaque metal or a metal which produces an enhanced ultrasound image. One potential problem with known endoluminal prostheses having such dissimilar metals is that a substantial difference in Electromotive Force (EMF) of adjacent metallic materials may promote corrosion. To avoid this problem, the present invention provides endoluminal prostheses with frames and marker element having similar EMF characteristics. A particularly preferred combination combines frames which include Nitinol® and marker elements which include tantalum. These materials exhibit excellent strength and imagability, respectively, and are of sufficiently similar characteristics to avoid electrolytic corrosion.

Figure 6:
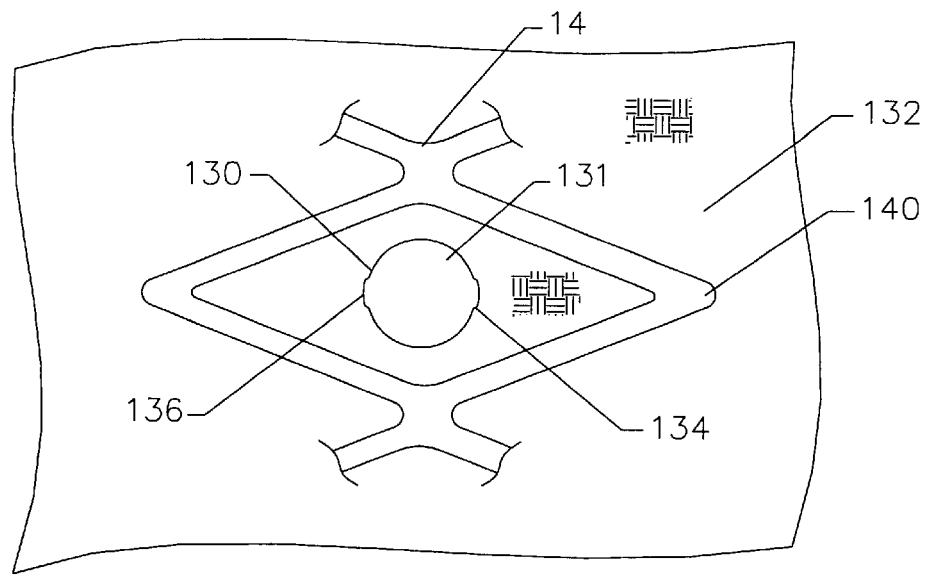
FIGS. 6–6B illustrate a preferred radiopaque marker element comprising an imagable body in the form of a plate having fastening shanks to facilitate attachment of the plate to the liner.
Figure 6A:
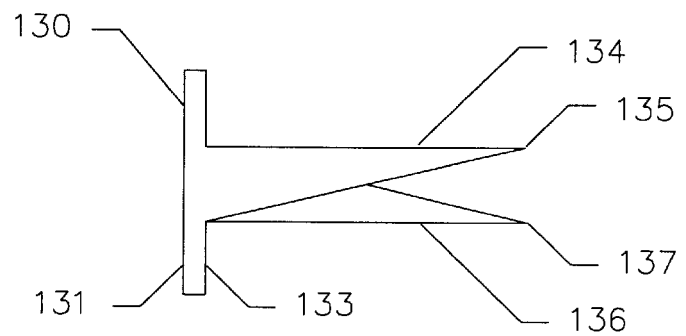
Figure 6B:
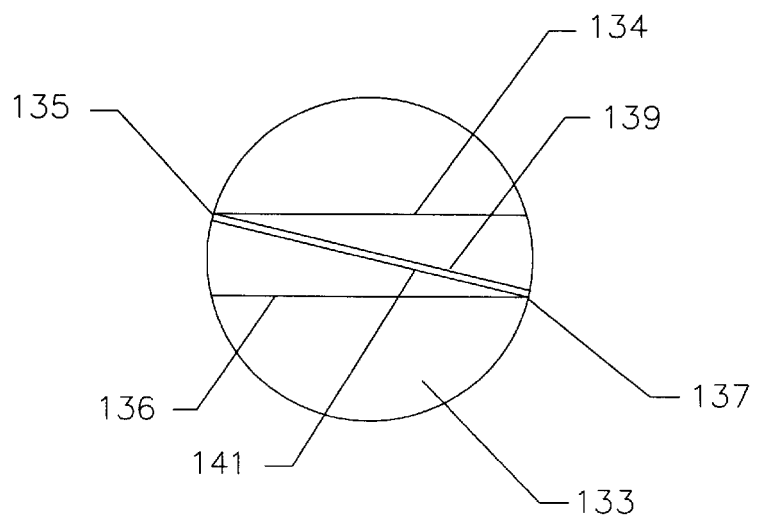

A preferred marker element structure comprising an imagable body attached to the liner will be described with reference to FIGS. 6–6B. The imagable body 30 here comprises a plate 130 attached to liner 132. Plate 130 includes two opposed major surfaces 131 and 133 and at least two fastening members or shanks 134 and 136 to facilitate the attachment. Plate 130 and shanks 134 and 136, generally comprise a material which provides a high sharp contrast when imaged, so as to indicate the liner position when the prosthesis is imaged within the patient body. Plate 130 typically includes a radiopaque material such as gold, platinum, or other implantable metals. Ideally, plate 130 comprises tantalum having a thickness of at least about 0.002 inches, preferably being about 0.01 inches. Such tantalum plates may be mass produced by die cutting or laser cutting sheet stock. In most embodiments, the edges of plates 130 will be rounded to avoid any injury to adjacent tissues, and to avoid cutting any liner or attachment fibers.

The plates are often attached to the outer surface of the liner material to avoid interference with the vascular flow or the generation of thrombus. Advantageously, where the liner is also supported by an external frame 140, the prosthetic lumen remains uninterrupted. Furthermore, where the plates are generally attached along a radius of the liner, they should not substantially interfere with expansion of the liner material.

Plate 130 may include a variety of alternative shapes. For example, plate 130 could be shaped as, but is not limited to, a square, a triangle, an oval, an arrow, a number or a letter. Each shape may correspond to a different application or need. Referring back to FIG. 5A, for example, a port orientation indicator 92 could be shaped as a circular disk, while gates 96 may be shaped as ovals. Still other marker elements 82 may have plates shaped as arrows to indicate deployment and/or blood flow direction.

Regardless of the shape of plate 130, the imagable bodies should be securely and reliably fastened to liner 132. Referring again to FIGS. 6A and 6B, as previously mentioned, the imagable bodies includes at least two shanks 134 and 136. Preferably, shanks 134 and 136 are made integral with plate 130. However, the shanks may be separately formed and attached to plate 130 using conventional adhesives techniques such as welding and the like. The shanks 134 and 136 provide the primary means for affixing the imagable body to liner 130. Optionally, however, the shanks can be used to affix marker 82 to external frame 140 within the scope of the present invention.

In a preferred embodiment, each shank 134 and 136 projects outward from plate 130. Shanks 134 and 136 are bent over, in the same direction, at right-angles to plate 130. The cantilevered end of the shanks 135 and 137 each end at a point sufficiently sharp enough to pierce fabric liner 132 without collapsing the shank upon the application of pressure to the marker. Once the shanks pierce liner 132, they are pushed through the liner until second major surface 133 is disposed adjacent liner 132. The shanks are then bent over in a direction toward the center of plate 130, until the shanks are generally parallel to major surface 133. Advantageously, each shank 134 and 136 is cut at right and eft opposing angles 139 and 141 so that the shanks lay side-by-side, substantially in the same plane, when the shanks are bent over parallel to the plate.

Referring now to FIG. 7, one exemplary method for installing the radiopaque marker elements to the liner of an endoluminal prosthesis includes using an installation tool 200. Installation tool 200 is generally formed of two opposed clamping members 202 and 204. One clamping member has a recessed portion 206 capable of receiving major surface 131 of plate 130. The second clamping member 204 has a recessed portion 210 that is designed with a surface feature capable of receiving shanks 134 and 136. In operation, marker 82 is positioned over a predetermined location on liner 132. Shanks 134 and 136.are forced to pierce liner 132 and pushed through until major surface 133 is disposed proximate to the liner. The clamping members 202 and 204 are then placed over marker 82 and plate 130 is inserted into recessed portion 206. A clamping force is then brought to bear on plate 130 and shanks 134 and 136 in the directions of arrows 208. The surface features of recessed portion 210 are designed to bend shanks 134 and 136 in a direction towards the center of plate 130 until desired or until the shanks are generally parallel to plate 130. As a result of the clamping, liner 132 is bound between the bent over shanks and major surface 133. Advantageously, except for the clamping tool, nothing else is needed to secure marker 82 to liner 132. Therefore, adhesives, sutures, or other attachment means are not necessary.

Although the exemplary embodiments have been described in some detail, by way of illustration and example, the scope of the present invention is limited solely by the appended claims.

What is claimed is:

1. An endoluminal prosthesis comprising:
   fabric liner comprising a polyester fabric; and
   an imagable body disposed on the liner, the body including a plate and at least two shanks integral with the plate, the shanks affixing the imagable body on the liner, the imagable body providing a sharp contrast so as to indicate the liner position when the prosthesis is imaged within the patient body.

2. A prosthesis as claimed in claim 1, wherein the fabric liner comprises a tubular graft having a proximal end, a distal end, and a lumen therebetween.

3. A prosthesis as claimed in claim 2, further comprising a radially expandable frame supporting the tubular graft.

4. A prosthesis as claimed in claim 1, wherein the plate comprises a shape taken from the group consisting of a square, rectangle, circle, triangle, arrow, and oval.

5. A prosthesis as claimed in claim 1, wherein the imagable body is radiopaque.

6. A prosthesis as claimed in claim 1, wherein each shank projects from an opposing edge of the plate and through the liner, the shanks bent over so as to attach the imagable body to the liner.

7. A prosthesis as claimed in claim 1, wherein each shank is cut at right and left opposing angles so that the arms lay side-by-side when the shanks are bent toward each other along the plate.

8. A prosthesis as claimed in claim 1, wherein the plate comprises first and second opposed major surfaces, wherein the shanks extend from the second major surface, and wherein the second major surface is disposed adjacent the liner.

9. A prosthesis as claimed in claim 1, wherein the shanks each comprise a pointed end capable of piercing the fabric liner.

10. An endoluminal prosthesis for deployment in a body lumen of a patient body the prosthesis comprising:
    a tubular fabric liner having a proximal end, a distal end, and a lumen therebetween; and
    a plurality of imagable bodies attached to the liner, each imagable body having a plate and two integral fastening members to attach of the imagable bodies to the liner, the imagable bodies providing a sharp contrast to define a pattern so as to indicate the prosthesis position when the prosthesis is imaged within the patient body.

11. A prosthesis as claimed in claim 10, further comprising a radially expandable frame supporting the liner.

12. A prosthesis as claimed in claim 11, wherein the frame comprises a tube defining a plurality of radial openings when expanded, and wherein images of at least some of the imagable bodies are visible through associated openings of the expanded frame.

13. A prosthesis as claimed in claim 10, wherein the plate comprises first and second opposed major surfaces, wherein the fastening members extend from the second major surface, and wherein the second major surface is disposed adjacent the liner.

14. A prosthesis as claimed in claim 10, wherein each fastening member is cut at right and left opposing angles so that the members lay side-by-side when the arms are bent over in the same direction parallel to the plate.

15. A prosthesis as claimed in claim 10, wherein the imagable bodies are radiopaque.

16. A prosthesis as in claim 10, wherein the plate comprises a material taken from the group consisting of tantalum, platinum, and gold.

17. A prosthesis as claimed in claim 10, wherein the imagable bodies provide enhanced ultrasound images.

18. An endoluminal prosthesis for deployment in a body lumen of a patient body, the prosthesis comprising:
- a tubular fabric liner having a proximal end, a distal end, and a lumen therebetween;
- a radially expandable frame supporting the liner; and
- a plurality of radiopaque marker elements, each marker element comprising a plate having a first and a second opposed major surface, with two fastening members extending from the second major surface, through the liner, and along the plate so as to affix the marker element to the liner, the marker elements indicating a position of the prosthesis when the prosthesis is imaged within the body lumen.

19. A prosthesis as in claim 18, wherein the marker elements are not directly attached to the frame.

20. A prosthesis as in claim 18, wherein the marker elements are not in contact with the frame when the frame is radially expanded.

21. A method for fabricating a stent-graft, the method comprising:
- affixing a marker plate to a liner by piercing the liner with a pair of shanks, the shanks extending from the plate, and bending the shanks; and
- supporting the liner with a radially expandable frame.

* * * * *